United States Patent
Vetter et al.

(10) Patent No.: US 10,456,563 B2
(45) Date of Patent: Oct. 29, 2019

(54) STEERABLE, CONFORMABLE, DRUG ELUTING BALLOON CATHETER

(71) Applicant: TransMed7, LLC, Portola Valley, CA (US)

(72) Inventors: Eugene H Vetter, Portola Valley, CA (US); James W Vetter, Portola Valley, CA (US); Alisen E Vetter, Shoreview, MN (US)

(73) Assignee: TransMed7, LLC, Portola Valley, CA (US)

( * ) Notice: Subject to any disclaimer, the term of this patent is extended or adjusted under 35 U.S.C. 154(b) by 0 days.

(21) Appl. No.: 15/059,904

(22) Filed: Mar. 3, 2016

(65) Prior Publication Data

US 2017/0056628 A1   Mar. 2, 2017

Related U.S. Application Data

(60) Provisional application No. 62/128,438, filed on Mar. 4, 2015.

(51) Int. Cl.
| | | |
|---|---|---|
| *A61M 25/10* | (2013.01) | |
| *A61M 25/01* | (2006.01) | |
| *A61B 17/32* | (2006.01) | |
| *A61M 25/00* | (2006.01) | |
| *A61N 5/10* | (2006.01) | |

(52) U.S. Cl.
CPC ......... *A61M 25/1011* (2013.01); *A61B 17/32* (2013.01); *A61M 25/0054* (2013.01); *A61M 25/0155* (2013.01); *A61N 5/1002* (2013.01); *A61M 2025/0057* (2013.01); *A61M 2025/105* (2013.01); *A61M 2205/02* (2013.01)

(58) Field of Classification Search
CPC .......... A61N 5/1002; A61N 2005/1003; A61N 2005/1005
USPC ............................................................ 600/3
See application file for complete search history.

(56) References Cited

U.S. PATENT DOCUMENTS

| | | | | |
|---|---|---|---|---|
| 4,744,366 | A | | 5/1988 | Jang |
| 5,514,115 | A | * | 5/1996 | Frantzen ........ A61B 17/320783 604/531 |
| 5,643,171 | A | * | 7/1997 | Bradshaw ......... A61M 25/1002 600/1 |
| 5,653,736 | A | | 8/1997 | Glastra |
| 5,855,546 | A | * | 1/1999 | Hastings ........... A61M 25/0127 600/3 |

(Continued)

OTHER PUBLICATIONS

Shore Hardness Scale, printed from internet Jan. 2, 2019, 1 page includes Shore OO, A and D. (Year: 2019).*

(Continued)

*Primary Examiner* — Samuel G Gilbert
(74) *Attorney, Agent, or Firm* — Young Law Firm, P.C.

(57) ABSTRACT

A steerable, conformable, drug eluting balloon catheter device may include a catheter stem with one or more balloon element(s), themselves comprised of one or more segment(s) arranged radially or axially along the length of the present catheter device may allow precise deployment of vascular interventional devices, including coring devices and/or placement of stents, and may also allow targeted, specific placement of selected diagnostic or therapeutic materials on the walls of a vascular structure during a cardiovascular intervention procedure.

19 Claims, 2 Drawing Sheets

(56) References Cited

U.S. PATENT DOCUMENTS

| | | | | |
|---|---|---|---|---|
| 5,910,101 | A | * 6/1999 | Andrews | A61N 5/1002 600/3 |
| 5,938,582 | A | * 8/1999 | Ciamacco, Jr. | A61N 5/1002 600/3 |
| 5,947,924 | A | * 9/1999 | Liprie | A61M 25/1002 604/103.07 |
| 6,117,064 | A | * 9/2000 | Apple | A61N 5/1002 600/1 |
| 6,273,876 | B1 | 8/2001 | Klima et al. | |
| 6,482,142 | B1 | * 11/2002 | Winkler | A61N 5/1015 600/3 |
| 6,491,617 | B1 | * 12/2002 | Ogle | A61F 2/82 600/3 |
| 6,508,784 | B1 | * 1/2003 | Shu | A61N 5/1002 600/3 |
| 2002/0026149 | A1 | 2/2002 | Agro et al. | |
| 2010/0168665 | A1 | 7/2010 | Skerven | |
| 2014/0046254 | A1 | 2/2014 | Stankus et al. | |
| 2014/0052105 | A1 | 2/2014 | Hattangadi et al. | |

OTHER PUBLICATIONS

Dictionary.com definition of interstitial, printed Aug. 14, 2019, 6 pages. (Year: 2019).*
Dictionary.com definitions of interstices, printed Aug. 14, 2019, 6 pages. (Year: 2019).*
Dictionary.com definitions of constriction, printed Aug. 14, 2019, 6 pages. (Year: 2019).*
International Search Report and Written Opinion dated May 16, 2016 in PCT/US16/020711.

* cited by examiner

STEERABLE, CONFORMABLE, DRUG ELUTING BALLOON CATHETER

BACKGROUND

Embodiments relate to medical devices and methods. More particularly, embodiments relate to a steerable, conformable, drug eluting balloon catheter medical device (hereinafter referred to as a balloon catheter) and methods of use of such a device in vascular interventional procedures.

SUMMARY

Embodiments are drawn to medical devices and methods that are used for vascular intervention procedures. Embodiments may comprise structures and functionality for balloon catheter intravascular placement, selective balloon element segment inflation, drug elution, conformability to a vascular structure in consonant use with another interventional device or delivery system, placement of stents, or transducer functionality. Embodiments may be portable, disposable or reusable and may be electrically, mechanically, hydraulically and/or manually powered and operated. The devices in this description include components that may be used together or separately to accomplish various vascular interventions in diseased vessels, where the disease encroaches on the luminal cross-sectional area of a vessel that limits flow through the vessel or vessels, or that results in unstable or ectatic segments at risk for rupture.

DETAILED DESCRIPTION

Figure 1:
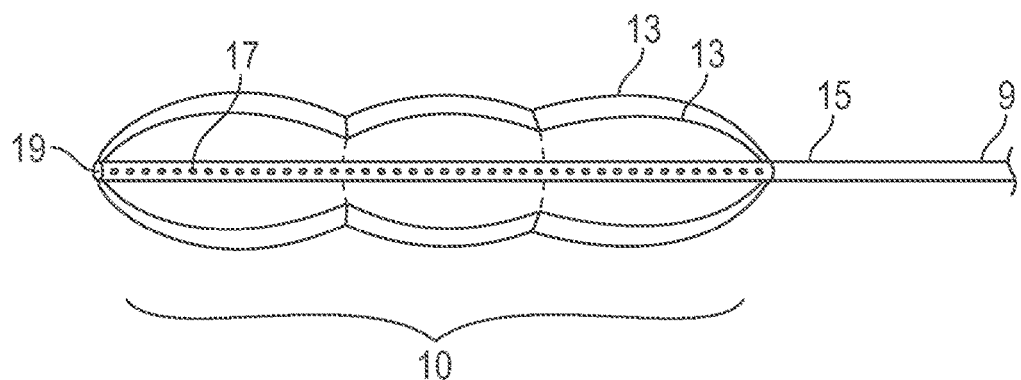
FIG. 1 is a side view of an inflated balloon catheter device, with a balloon element having one or more segmented parts, according to one embodiment.

The following description is only exemplary of the embodiments described and shown herein. The embodiments of the present balloon catheter device, therefore, are not limited to these implementations, but may be realized by other implementations. Although the use of this device is described principally in terms of vascular interventional procedures, embodiments of the present device may be advantageously used in any procedure within a tubular shaped structure in the body, including gynecologic, urologic, orthopedic, thoracic and other soft tissue procedures, for example.

Percutaneous procedures such as transluminal angioplasty and transluminal atherectomy seek to increase downstream blood flow by improving the cross-sectional diameter of a vessel affected by a common process of vascular wall disease that over time significantly thickens the walls of these vessels, often asymmetrically. The process of luminal cross-section reduction can also occur suddenly when unstable disease bulk ruptures abruptly causing thrombus formation and often, total occlusion of the affected artery resulting in significant muscle and nerve damage and destruction in the vessel outflow areas.

Many technologies have been developed to treat these areas, either to remodel the diseased walls of vessels through dilatation (transluminal angioplasty) or removal of some of the bulk (transluminal atherectomy) both of which procedures may be followed by scaffolding the walls with implanted devices that may be permanent (stents) or may be removed or dissolve themselves over time (temporary stents). These devices may also be coated with various drugs to limit re-narrowing of the vessel lumen that commonly occurs during the healing process. The limitations of the current technologies are well known and widely reported.

The technologies described herein are designed to overcome many of the limitations of current technologies, mainly focusing on ease of delivery of devices into the vascular areas of disease, more effective treatment of the diseased areas, particularly in areas of asymmetry of disease, more precise treatment endpoints with these devices and methods, less trauma in treatment areas as well as areas collateral to treatment sites, enhanced safety at the treatment sites as well as areas distal to the diseased segments and additionally, improved efficiency of the procedures using the embodiments and methods detailed in this submission. The foregoing are general capabilities of the devices and methods; more specific device and method capabilities will become apparent upon study of the following descriptions and drawings of embodiments.

Embodiments of the present steerable, conformable, drug-eluting balloon catheter may be useful for guiding and placement of any generic vascular interventional device via the enclosed central lumen of the balloon catheter, such as, for example, an intravascular coring device for specific, targeted remodeling of diseased areas within a vascular structure during a percutaneous vascular interventional procedure. Embodiments of the present balloon catheter device may also be useful for guiding appropriately sized generic imaging technology such as intravascular ultrasound instruments, flow reserve instruments and others through a vascular structure. Embodiments of the present balloon catheter device may also be useful for guiding and placement of an enclosed central lumen-located generic intravascular device for delivery of diagnostic or therapeutic materials such as, for example, medications, brachytherapy agents, dyes, or markers to a specific, targeted area of a vascular structure. Embodiments of the present balloon catheter device may also be useful in the placement of stents or in eluting one or more selected medications to specific parts of a vascular structure. Embodiments of the present balloon catheter device may also be useful in sensing vascular wall compliance. Embodiments of the present balloon catheter device may have strain gauges attached to or imbedded in a balloon element(s) to detect the amount of stretch on a balloon element(s) wall during balloon elements(s) inflation, and transmit such sensed information to the operator, according to methods. Embodiments of the present balloon catheter device may have transducers attached to or imbedded in a balloon element(s) to detect, for example, pressure during balloon elements(s) inflation, and transmit such sensed information to the operator, according to methods. Embodiments of the present balloon catheter device may have a balloon element(s) having walls coated with or comprising textured materials such as, for example, nanomaterials with a directional "fish-scale" pattern(s) enabling maximum stabilization of the present balloon catheter device within a vascular structure as such a balloon element(s) is inflated and anchors to the vessel wall, according to methods. Embodiments of the present balloon catheter device may have multiple balloon elements having different diameters upon maximum inflation which are arranged in alternate or staggered locations radially and axially along the stem of the present balloon catheter device, such that one balloon element may provide anchoring capability while another balloon element of smaller size may move farther through the vascular structure into areas that may be more difficult to access, such as, for example, a smaller branch vessel or an area of the vessel having thicker disease tissue associated with its walls, according to various methods. Embodiments of the present balloon catheter device may have exit fenestrations placed in various locations such that other devices useful for delivery of pharmacologic agents and other devices such as wires, imaging devices and the like may be directed towards a specific location in a vascular tree for example, such as a side branch, around an area of obstruction and other challenging anatomic phenomena. Embodiments of the present balloon catheter device may be configured with any number of features described herein, including, for example, having one or more of a balloon element(s) whether segmented or whole, placed sequentially along a balloon catheter device, depending on the intended use of the device. Embodiments of the present balloon catheter device may have a balloon element(s) comprising one or more segment(s) that may be of any useful size and shape and may be arranged in any spatial configuration including, for example, radially, perpendicularly, axially, longitudinally or at any angle with respect to the balloon catheter stem. Embodiments of the present balloon catheter device may have a central lumen of any length that may be flexible and may have any useful internal and external diameter with any luminal shape.

Reference will now be made in detail to the construction and operation of embodiments illustrated in the accompanying drawings. FIG. 1 shows a side perspective view of a steerable, conformable, drug-eluting balloon catheter device. In this figure, the distal end of the balloon catheter device 9 is shown having a balloon element 10 with multiple, individually inflatable segments 13 in a partially or fully inflated state arranged both longitudinally and axially along a central catheter stem 15, according to one embodiment, with drug eluting holes 17 located in elution segments 18 (not shown in this view) along the axial length of the catheter between the balloon element segments 13, according to one embodiment. Alternatively, according to another embodiment, the drugs to be delivered may be in the form of a pre-coated gel located between the balloon element segments 13 axially along the length of the catheter stem 15, in which case they may be squeezed outward radially when the balloon element segments 13 are inflated. The catheter stem 15 may be of any length, be flexible, and may be constructed internally of a number of radial segments, some of which may be devoted to inflation of specific balloon element segments 13 and others of which may be devoted to eluting a single drug to all elution segments 17 or selected drugs to different elution segments 17 radially separated from each other and located between the portions of the balloon element segments 13, according to embodiments. Central to these radial segments may be a central lumen 19 through which may be passed an independently movable generic guiding element such as a shapeable wire 21 (not shown in this figure) or any appropriately sized generic vascular interventional device 23 (not shown in this figure). A central lumen 19 may also house (not shown in this figure) independently movable, appropriately sized generic imaging technology such as intravascular ultrasound instruments, flow reserve instruments and others, or any appropriately sized generic diagnostic or therapeutic delivery technology used for medication or brachytherapy agent delivery, dye injection or placement of markers, according to various methods. A central lumen (conduit) may also have one or more exit points along its length to permit directional delivery of any of the above devices as well as pharmacologic agents, as well as brachytherapy agents such as seeds, radioactive wires and the like.

The central conduit may itself be constructed such that it may surround an additional coaxial central lumen, expand as a balloon element (not shown) and may be used to express pharmacologic agents outward between radially disposed balloons or in the case of it being coaxially in direct contact with one or more outer balloons, it may displace contents from one or more outer balloons through specially constructed fenestrations in the one or more outer balloons, into the wall of a vessel, creating another pathway and mechanism for drug delivery according to another embodiment.

Figure 2:
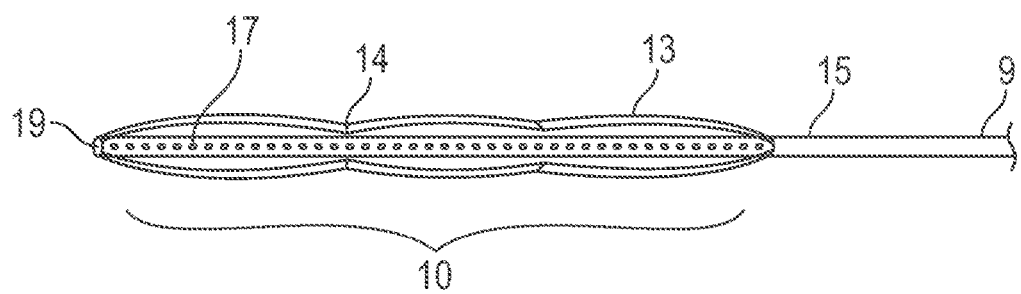
FIG. 2 is a side view of a deflated balloon catheter device, with a balloon element having one or more segmented parts, according to one embodiment.

FIG. 2 represents a side perspective view of a balloon catheter device 9 with a balloon element 10 having segments 13 nearly or completely deflated, according to one embodiment. In this figure, a catheter stem 15, drug elution holes 17 and central lumen 19 of the device are visible. In this figure, the flexible balloon catheter device 9 is straight along its axial length. Any number of segments with interstitial constrictions 14 may be found in each of the radially located balloon element segments 13 around the catheter stem 15. These individual balloon element segments 13 may be of use in selectively deforming the catheter stem 15 in X and Y radial directions in conjunction with rotation of the whole balloon catheter device 9 in order to steer the distal tip of the balloon catheter in any desired direction, according to embodiments and methods. Such a steering function may be of use for ease of movement through a vascular structure while also accommodating its inner diameter. Such a steering function of the present device 9 may also be of use in painting therapeutic or other selected agents on targeted, specific portions of a vascular structure in a positive and discriminating manner, including symmetric or asymmetric application as indicated.

Figure 3:
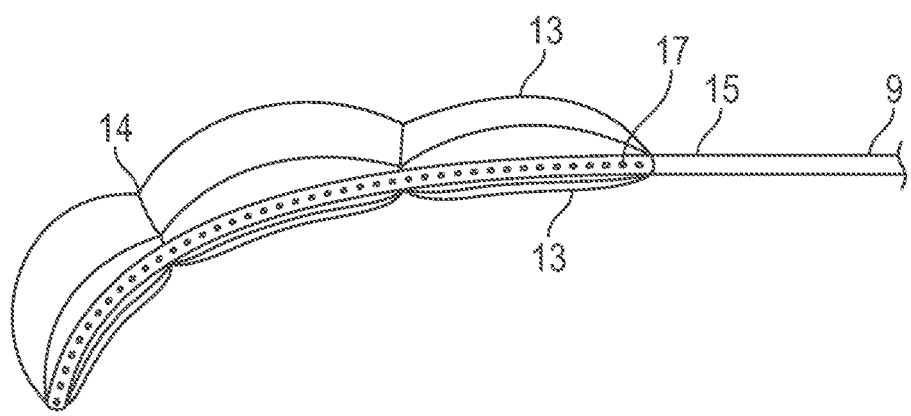
FIG. 3 is a side view of a selectively inflated balloon catheter device, with a balloon element having more than one segmented parts, according to one embodiment.

FIG. 3 represents a side perspective view of the present balloon catheter device 9 with partially inflated balloon element 10 segments 13, according to one embodiment. In this view, the upper balloon element 10 segments 13, themselves separated into lobes by their interstitial constrictions 14, may be seen to be at least partially inflated while those lower balloon element 10 segments 13 may be seen to be deflated and may also have vacuum applied to them via their respective intra-catheter stem 15 segmented channels (not shown in this view), according to embodiments. The selective applied hydraulic pressure in each of the balloon element segments 13 may tend to deform the tip of the device 9 and its central lumen 19 in a specifically desired direction during an interventional procedure, according to methods. If a specific balloon element 10 segment 13 is over-inflated, it may exert an opposite deformation force to the catheter stem 15 and efficiently point the distal tip in a desired direction, which may be of particular use if a generic vascular interventional device, such as a coring device, for example, is deployed in a central lumen 19 of the device 9 and from which it may be extended, according to methods.

Figure 4:
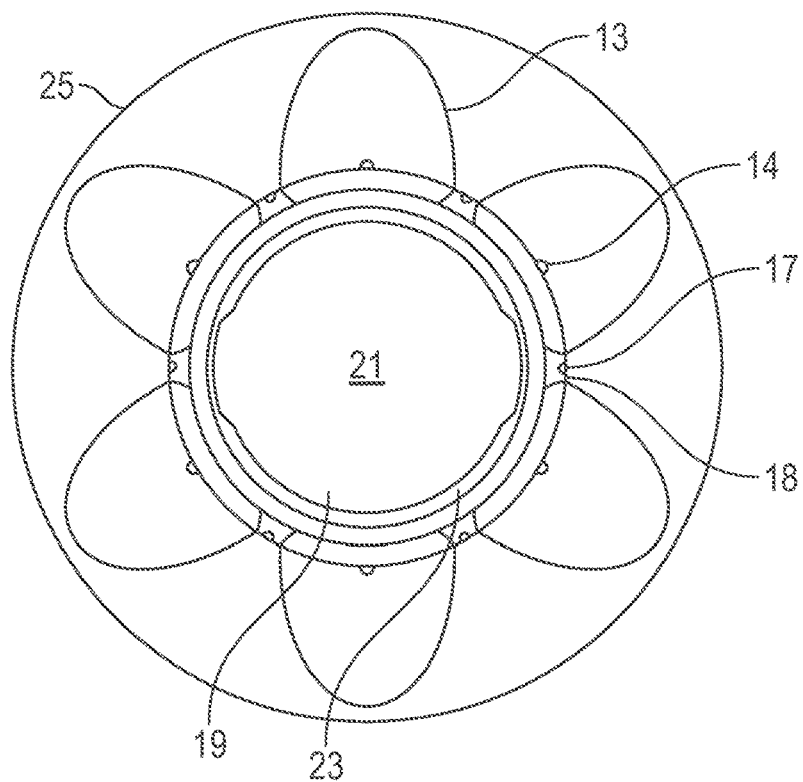
FIG. 4 is an end-on view of an inflated balloon catheter device in a vascular structure, with a balloon element having one or more segmented parts, according to one embodiment.

FIG. 4 represents an end-on perspective view of a balloon catheter device 9 within a vascular structure 25, according to one embodiment. In this view, the equally inflated balloon element 10 segments 13 may be seen disposed centrally to a vascular structure 25 with a generic vascular interventional device 23 placed within a central lumen 19 of the catheter stem 15. Also shown in the central lumen of the catheter stem is a guide wire 21, for purposes of illustration. In this view, individual catheter stem inflation channels 14 may be seen, and it should be noted that each radially arranged individual balloon element 10 segment 13 may also be divided into individual axial segments between the interstitial constrictions 14, each of which may have its own respective inflation channel, not shown but easily envisioned in this view. Combining the side view of FIG. 1 with this end view of FIG. 4, it may be envisioned that for six individual balloon element segments 13 disposed radially around a catheter stem 15, and with each individual balloon element segment 13 constricted axially into three individually inflatable segments, that there are a total of 18 inflatable cells that may allow an operator to radially deflect the distal end of a catheter stem 15 in both X and Y radial directions, according to various embodiments. Also shown in this view are drug elution channels 18 and drug-eluting holes 17 disposed between balloon element 10 segments 13. Each of the drug elution channels 18 may be provided with a selected drug, according to methods.

Figure 5:
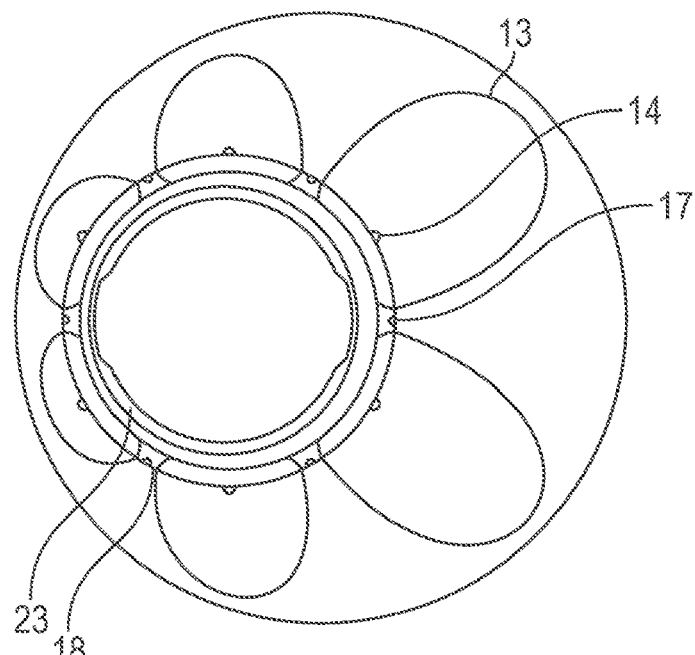
FIG. 5 is an end-on view of a selectively inflated balloon catheter device in a vascular structure, with a balloon element having more than one, segmented parts, according to one embodiment.

FIG. 5 represents an end-on perspective view of a balloon catheter device 9 within a vascular structure 25, according to one embodiment and method. In this figure, the elements of FIG. 4 are again represented, but in this view, selective inflation and over inflation on certain of the radially disposed balloon element 10 segments 13 result in the placement of a generic cardiovascular interventional device 23, such as a coring device deployed within a central lumen 19 of the catheter device 9, to be advantageously placed closer to one vascular wall than another, according to methods. Such placement may aid in selectively anchoring a coring device 23 within a vascular structure to effectively penetrate and remodel a difficult vascular lesion cap with precision, or to shave (de-bulk) diseased tissue from the vascular wall one layer at a time, while rotating the balloon catheter device 9 and/or moving the balloon catheter device in an antegrade or retrograde manner, with respect to blood flow, to position the coring tip of a generic interventional device 23, according to methods. It is assumed that a generic coring device 23 may be extended axially from the balloon catheter device 9 to perform its function, according to other methods. In addition to vascular applications, the characteristics described above may be used for asymmetric delivery of radiotherapy dosages in other tissue environments. Additionally, any of segmented balloon compartments may be differentially filled with shielding substances to further tailor a radiation dose in a desired direction, while limiting exposure of radiation to sensitive structures, including areas where active healing is desired such as percutaneous entry sites and other surgical access wounds.

The present balloon catheter device 9 may also advantageously be used for stent placement inside a vascular structure, and a stent (not shown in the figures, but assumed to be pre-loaded onto the outside of a balloon element(s) 10 segment(s) 13 of the device 9) may be specifically matched to the regularly or irregularly shaped inner surface of a vascular structure (or surgical cavity) by selectively inflating individual balloon element(s) 10 or balloon element(s) 10 segment(s) 13, according to embodiments and methods. Drugs may be eluted in certain or all balloon element(s) 10 and balloon element(s) 10 segment(s) 13 before, during, or after stent placement and expansion procedures, according to methods.

One embodiment is a method of precisely deploying independently movable, appropriately sized generic imaging technology such as intravascular ultrasound instruments, flow reserve instruments and others, or any independently movable, appropriately sized generic diagnostic or therapeutic delivery technology used for medication or brachytherapy agent delivery, dye injection or placement of markers, according to various methods, through a central lumen 19 of a catheter stem 15 of the steerable, conformable balloon catheter device 9. The balloon catheter device 9 may be steered to a selected portion of a vascular structure by selectively applying and withdrawing hydraulic pressure, for example, in each of the balloon element(s) 10 or balloon element(s) segment(s) 13 to exert a deformation force to a catheter stem 15 and efficiently point the distal tip of the balloon catheter device 9 in a desired direction in order to aid travel through a vascular structure to the desired area of the vessel. Additionally, inflation of a balloon element(s) 10 or balloon element(s) 10 segment(s) 13 may be accomplished to conform to the vessel walls and anchor the balloon catheter device 9 in place. Further selective application and withdrawal of hydraulic pressure, for example, in each of the balloon element segments 13 to exert a deformation force to a catheter stem 15 may then be accomplished to direct the distal tip of the balloon catheter device 9 to a specified area(s) of the vascular wall and thus direct the working end of a generic delivery technology to the area(s) for specific, directional, movement for precise placement of a marker, for example, or precise symmetric or asymmetric application of medication to a specific area of the vascular wall, according to methods.

Another embodiment is another method of applying one or more drugs in a discriminating manner to a specific area(s) of a vascular wall by deploying a steerable, conformable, drug-eluting balloon catheter device 9 to a selected portion(s) of a vascular structure, followed by inflation of a balloon element(s) 10 or balloon element(s) 10 segment(s) 13 to conform to the vessel walls and anchor the balloon catheter device 9 in place and then applying one or more drugs to a selected area(s) of the vessel wall by initiating drug elution from a selected, pre-drug-loaded balloon element(s) 10 or balloon element(s) 10 segment(s) 13 of the balloon catheter device 9, or through the central lumen of the balloon catheter itself, which may be equipped with a directional eluting tip, according to various embodiments and methods.

Another embodiment is a method of carrying out a de-bulking vascular interventional procedure by deploying a steerable, conformable balloon catheter device 9 to a selected portion of a vascular structure, followed by inflation of a balloon element(s) 10 or balloon element(s) 10 segment(s) 13 to conform to the vessel walls upstream from the vascular lesion(s) and anchor the balloon catheter device in place, and then deploying within a central lumen 19 of a catheter stem 15 an independently movable, appropriately sized generic interventional coring device to remodel the diseased vascular wall in a selective manner. During an atherectomy procedure, the balloon catheter device 9 may serve to stabilize the vascular wall, allow blood flow to continue through a central lumen 19 or laterally around a balloon element(s) 10, direct the working end of the interventional coring device into the desired area(s) of the vascular wall at selected depths during the de-bulking procedure, and protect the vascular wall from movement of portions of the interventional coring device that are proximal or lateral to the working end of the coring device.

Another embodiment is a method of stent placement by deploying to a selected portion of a vascular structure a steerable, conformable, balloon catheter device upon which has been fixed one or more collapsed stent(s), drug eluting or otherwise. Upon appropriate placement of the balloon catheter device 9 within the vascular structure, inflation of a balloon element(s) 10 or balloon element(s) 10 segment(s) 13 is accomplished to expand and place the stent(s) in a manner that precisely conforms to the selected area(s) of the vascular wall.

Another embodiment is a method of gathering real-time data to indicate the size and shape of the internal wall of a vascular structure, whether healthy or containing diseased tissue, through the use of transducers (commercially available, not shown in the illustrations herein) attached to or imbedded in a balloon element(s) 10 or balloon element(s) 10 segment(s) 13 of the present balloon catheter device to detect and transmit, for example, pressure as a balloon element(s) is inflated against the vascular wall. Such sensed information may be transmitted to the operator by already commercially available means, including electronic or hard copy output from a pressure graph. Such output information may be useful to provide a map of the size and shape of an interior wall of a vascular structure, including if, for example, more advanced imaging technology is not available.

Another embodiment is a method of gathering real-time data regarding stretch of a balloon element(s) through the use of strain gauges (commercially available, not shown in the illustrations herein) attached to or imbedded in a balloon element(s) 10 or balloon element(s) 10 segment(s) 13 of the present balloon catheter device 9 to detect and transmit data regarding the amount of stretch on a balloon element(s) 10 or balloon element(s) 10 segment(s) 13 during inflation toward a vascular wall. Such data may enable, for example, the operator to direct the distal end of the present balloon catheter device toward a specific area of a vascular wall, according to the transmitted stretch data, for the purpose of delivery of diagnostic or therapeutic materials such as, for example, medications, brachytherapy agents, dyes, or markers to a specific, targeted area of a vascular structure, or for the purpose of directing a generic interventional atherectomy device to a specific, targeted diseased area of a vascular structure.

It is to be understood that the above descriptions are but exemplary methodologies and that one or more of the steps described above may be omitted, while other steps may be added thereto to any of these embodiments, depending on the intended use. Other operator method embodiments and device embodiments are supported as well. The order of some of the steps may additionally be changed, according to the desired procedure.

It should also be noted that, according to embodiments, any number of balloon element(s) 10 segments 13 of the present balloon catheter device 9 and constrictions of the balloon element segment(s) 13 may be configured as part of the balloon catheter device 9, and that placement of stents and/or location and anchoring of the coring tip of an interventional device 23 may be of particular use to an operator, since the balloon element segment(s) 13 may be inflated to accommodate a vascular structure's internal dimensions, both in place and while advancing the present balloon catheter device to a targeted interventional site, according to methods.

Dimensions of the balloon catheter device 9 may vary widely, and may follow commonly used dimensions such as French 4, 5 and 6, for example, and according to embodiments. It is to be understood, however, that the foregoing dimensions and any dimensions referred to herein are exemplary in nature only. Those of skill in this art will recognize that other dimensions and/or configurations may be implemented, depending upon the application, and that the elements of the device could be of any length or dimension, all of which are considered within the scope of this disclosure. Furthermore, any discussion of dimensions or ranges of dimensions or physical or dynamic aspects such as ranges of motion or time factors outlined herein are exemplary in nature only and should not be considered to be limiting.

The entire present balloon catheter device may be configured to be disposable or may be configured to be reusable in whole or in part. Embodiments of the present device may be, for example, hydraulically powered or electrically powered by one or more batteries and/or external power sources through an electrical coupling to connect to an external power supply conveniently placed, for example, in the handle or proximal end of the present biopsy device. The entire device may also be internally or externally manually powered, mechanically powered. Powering the device entirely mechanically may be advantageous in areas in which the electric grid is absent, unavailable, or unreliable. A power source may comprise an external commercially available AC to DC transformer approved for medical device use and plugged into a provided socket in the present balloon catheter device, or may comprise an enclosed battery of any suitable and commercially available power source. Additionally, other power sources, for example, mechanical linkages or compressed fluid motors or vacuum systems may be used. Individual components of the present balloon catheter device may be formed of or comprise one or more biocompatible materials such as, for example, stainless steel or other biocompatible alloys, and may be made of, comprise or be coated with polymers, such as polyimide, for example, and/or biopolymer materials as needed to optimize function(s). Balloon elements may be constructed of any of a number of high strength, stretchable polymers, compounds and composite materials, and may contain high strength fibers laid in patterns that enhance or maximize their intended inflated and deflated shapes and conformation. Some of the components may be purposely surface-treated differentially with respect to adjacent components, as detailed. The handle of the present device may likewise be made of or comprise plastic such as injection-molded, for example, or other suitable rigid, easily hand-held strong and light-weight material. The handle may be configured in such a way as to make it easily adaptable to one of any number of existing guiding platforms, such as stereotactic table stages. The materials used in the present balloon catheter device may also be carefully selected from a ferro-magnetic standpoint, such that the present device maintains compatibility with MRI equipment.

While certain embodiments of the disclosure have been described, these embodiments have been presented by way of example only, and are not intended to limit the scope of the disclosure. Indeed, the novel methods, devices and systems described herein may be embodied in a variety of other forms and other applications. All such other applications making use of the principles disclosed herein for this device and that could be envisioned by one skilled in the art are therefore considered to be within the scope of this disclosure. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments the actual physical and logical structures and dimensions thereof may differ from those shown in the figures. Depending on the embodiment, certain steps described in the example above may be removed while others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments, which do not provide all of the features and advantages set forth herein, are also within the scope of this disclosure. Accordingly, the scope of the present disclosure is intended to be defined only by reference to the appended claims.

What is claimed is:

1. A device, comprising:
a bendable central catheter stem;
a plurality of balloon elements disposed radially around the bendable central catheter stem, each balloon element of the plurality of balloon elements comprising a plurality of spaced-apart interstitial constrictions, the plurality of spaced-apart interstitial constrictions of each of the plurality of balloon elements defining a plurality of balloon segments that are immediately adjacent to one another and that extend from near a distal tip of the bendable central catheter stem to a distance proximal to the distal tip; and
a plurality of inflation channels disposed within the bendable central catheter stem, each of the plurality of inflation channels being configured to individually inflate a respective one of the plurality of balloon segments of each of the plurality of balloon elements radially disposed around the bendable central catheter stem,
wherein each balloon segment of the plurality of balloon segments of each balloon element of the plurality of balloon elements disposed radially around the central catheter stem is selectably and individually inflatable by selective application and withdrawal of hydraulic pressure to cause each to exert a deformation force and cause the central catheter stem to selectively bend and conform to a shape of a vascular wall, and wherein at least a portion of the plurality of spaced-apart interstitial constrictions are further away from the bendable central catheter stem when the plurality of balloon segments are inflated than when the plurality of balloon segments are uninflated.

2. The device of claim 1, wherein a number of the plurality of individually inflatable balloon segments is equal to a number of the radially-disposed plurality of balloon elements multiplied by a number of plurality of individually inflatable balloon segments per balloon element of the plurality of balloon elements.

3. The device of claim 1, wherein at least one of the plurality of balloon elements is coated with a drug.

4. The device of claim 1, wherein the bendable central catheter stem comprises a surface defining a central catheter stem lumen.

5. The device of claim 4, wherein the central catheter stem lumen is configured to accommodate a tissue cutting device and to enable the tissue cutting device to emerge from a distal end of the central catheter stem lumen.

6. The device of claim 1, wherein the bendable central catheter stem further comprises a plurality of openings configured to deliver a therapeutic substance.

7. The device of claim 6, wherein at least some of the plurality of openings are disposed between adjacent ones of the plurality of individually inflatable balloon segments.

8. The device of claim 1, wherein the central catheter stem comprises a plurality of flexible radial segments.

9. The device of claim 1, wherein at least one of the plurality of individually inflatable balloon segments comprises radiation-shielding properties.

10. The device of claim 1, wherein the plurality of individually inflatable balloon segment are selectively fully and partially inflatable and are selectively and individually fully and partially deflatable.

11. The device of claim 1, wherein the bendable central catheter stem is configured to enable continued blood flow when the device is inserted in a blood vessel.

12. A method, comprising:
providing a steerable and conformable balloon catheter device that comprises a bendable central catheter stem and a plurality of balloon elements disposed radially around the bendable central catheter stem, each balloon element of the plurality of balloon elements comprising a plurality of spaced-apart interstitial constrictions, the plurality of spaced-apart interstitial constrictions of each of the plurality of balloon elements defining a plurality of balloon segments that are immediately adjacent to one another and that extend from near a distal tip of the bendable central catheter stem to a distance proximal to the distal tip of the bendable central catheter stem, the balloon catheter device further comprising a plurality of inflation channels disposed within the bendable central catheter stem, each of the plurality of inflation channels being configured to individually inflate a respective one of the plurality of balloon segments of each of the plurality of balloon elements radially disposed around the bendable central catheter stem,
inserting the balloon catheter into a vasculature;
selectively inflating at least one of the plurality of individually-inflatable balloon segments through a corresponding at least one of the plurality of inflation channels, to apply pressure against a wall of the vasculature and cause the bendable central catheter stem to bend radially away from the at least one inflated balloon segment of the plurality of individually-inflatable balloon segments to cause the catheter device to conform to a shape of and steer through the vasculature, wherein at least a portion of the plurality of spaced-apart interstitial constrictions are further away from the bendable central catheter stem when the plurality of balloon segments are inflated than when the plurality of balloon segments are uninflated.

13. The method of claim 12, further comprising selectively applying and withdrawing hydraulic pressure to at least some of the plurality of individually-inflatable balloon segments.

14. The method of claim 12, further comprising selectively deflating at least one of the plurality of individually-inflatable balloon segments through a corresponding at least one of the plurality of inflation channels.

15. The method of claim 12, further comprising delivering a drug from at least one of openings in the bendable central catheter stem and from a material of the plurality of individually-inflatable balloon segments.

16. The method of claim 12, wherein providing is carried out with the bendable central catheter stem comprising a central catheter stem lumen and wherein the method further comprises:
- inserting a tissue cutting device through the central catheter stem lumen, at least a portion of the tissue cutting device emerging from a distal end of the central catheter stem;
- anchoring the catheter device against a wall of the vasculature by selectively inflating at least one of the plurality of individually-inflatable balloon segments; and
- cutting tissue using the tissue cutting device.

17. The method of claim 12, wherein providing is carried out with the central catheter stem comprising a plurality of flexible radial segments.

18. The method of claim 12, wherein at least one of the plurality of individually-inflatable balloon segments comprises radiation-shielding properties and wherein the method further comprises:
- delivering radiation to the vasculature while shielding portions of the vasculature facing the at least one of the plurality of individually-inflatable balloon segments that comprises radiation-shielding properties.

19. The method of claim 12, further comprising enabling blood flow through the bendable central catheter stem.

\* \* \* \* \*